US00PP20969P2

(12) United States Plant Patent
Klemm et al.

(10) Patent No.: US PP20,969 P2
(45) Date of Patent: Apr. 27, 2010

(54) POINSETTIA PLANT NAMED 'NPCW08119'

(50) Latin Name: *Euphorbia pulcherrima*
Varietal Denomination: NPCW08119

(75) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/316,345

(22) Filed: Dec. 11, 2008

(51) Int. Cl.
*A01H 5/00* (2006.01)

(52) U.S. Cl. ..... Plt./304

(58) Field of Classification Search ..... Plt./304
See application file for complete search history.

*Primary Examiner*—Kent L Bell
(74) *Attorney, Agent, or Firm*—Jondle & Associates, P.C.

(57) ABSTRACT

A new poinsettia plant particularly distinguished by an upright compact growth habit and a brilliant stable white bract color is disclosed.

1 Drawing Sheet

Genus and species: *Euphorbia pulcherrima* (Willd.).
Variety denomination: 'NPCW08119'.

BACKGROUND OF THE NEW PLANT

The present invention comprises a new and distinct cultivar of poinsettia plant, botanically known as *Euphorbia pulcherrima* (Willd.) and hereinafter referred to by the cultivar name 'NPCW08119'. The new cultivar is the result of an induced mutation by x-rays (30 Gy) of the parent poinsettia plant 'NPCW02044' (U.S. Plant Pat. No. 14,618) in November 2003 in Stuttgart, Germany.

The new cultivar has been asexually reproduced over twelve generations by vegetative cuttings in Stuttgart, Germany starting in spring 2004. The cultivar has proved to be stable and uniform. The present invention has been found to retain its distinctive characteristics through successive asexual propagations.

SUMMARY OF THE INVENTION

The following are the most outstanding and distinguishing characteristics of this new cultivar when grown under normal horticultural practices in Stuttgart, Germany.

1. Upright compact growth; and
2. Brilliant, stable white color;

DESCRIPTION OF PHOTOGRAPH

This new poinsettia plant is illustrated by the accompanying photograph which shows overall plant habit including cyathia buds, colored bracts and foliage of the plant; the colors shown are as true as can be reasonably obtained by conventional photographic procedures.

The photograph is of a whole plant about three-months-old grown in a greenhouse in Stuttgart, Germany.

DESCRIPTION OF THE NEW CULTIVAR

The following detailed description sets forth the distinctive characteristics of 'NPCW08119'. The data which define these characteristics were collected from asexual reproductions carried out in Stuttgart, Germany. The plant history was taken on on four-month-old plants with a minimum pinch date of 33 weeks. The plants were grown in a greenhouse covered with glass. Color readings were taken under natural light in the greenhouse. Color references are primarily to The R.H.S. Colour Chart of The Royal Horticultural Society of London (RHS) (2001).

DETAILED BOTANICAL DESCRIPTION OF THE NEW PLANT

Classification:
- *Family.*—Euphorbiaceae.
- *Botanical.*—*Euphorbia pulcherrima.*
- *Common.*—Poinsettia.
- *Variety denomination.*—'NPCW08119'.

Parentage:
- *Parent.*—'NPCW02044' (U.S. Plant Pat. No. 14,618).

Growth:
- *Time to produce a rooted cutting.*—3 to 4 weeks.
- *Blooming habit.*—Intermittent.
- *Flowering response time.*—Approximately 57 days.
- *Keeping quality.*—About 25 days.

Plant:
- *Form.*—Triangular.
- *Growth habit.*—Upright.
- *Height.*—25.0 cm to 30.0 cm.
- *Width.*—20.0 cm to 30.0 cm.
- *Number of branches.*—4 to 6.
- *Average number of inflorescences per plant.*—5.

Stems:
- *Color.*—RHS 143A.
- *Length.*—23.0 cm.
- *Internode length.*—1.0 cm to 3.0 cm.
- *Diameter.*—0.5 cm to 1.0 cm.

Leaves:
- *Quantity.*—8 to 15 per lateral branch.
- *Arrangement.*—Alternate.
- *Shape.*—Ovate.
- *Base.*—Obtuse.
- *Apex.*—Acute.
- *Lobes.*—Present, lobation is slight.
- *Margin.*—Serrate.

*Texture, both surfaces.*—Smooth.
*Vein color.*—Upper surface: RHS 144D. Lower surface: RHS 139D.
*Variegation.*—Absent.
*Size.*—Length: 4.0 cm to 10.0 cm. Width: 3.0 cm to 8.0 cm.
*Color.*—Mature foliage: Upper surface: RHS 139A to RHS 141A. Lower surface: RHS 139C. Immature foliage: Upper surface: RHS 141A. Lower surface: RHS 139C.
*Leaf petiole.*—Length: 2.0 cm to 4.0 cm. Diameter: 0.2 cm to 0.3 cm. Color: RHS 143C. Texture: Smooth.
*Aspect.*—Horizontally directed, leaf blades slanting somewhat downward.

Inflorescence:
*Blooming habit.*—Intermittent.
*Inflorescence type.*—Inflorescences are compound corymbs of cyathia with colored flower bracts subtending the cyathia.
*Lastingness on the plant.*—4 to 5 weeks.
*Diameter.*—17.0 cm to 23.0 cm.
*Height of inflorescence.*—3.0 cm to 5.0 cm.
*Fragrance.*—None.
*Natural flowering season.*—Autumn/winter; flower initiation and development is induced under short day/long night conditions.

Bracts:
*Number of bracts per inflorescence.*—6 to 7.
*Shape.*—Ovate.
*Base.*—Obtuse.
*Apex.*—Acute.
*Lobes.*—Present, lobation is slight.
*Size.*—Length: 7.0 cm to 12.0 cm. Width: 5.0 cm to 9.0 cm.
*Texture, both surfaces.*—Smooth.
*Vein color, both surfaces.*—RHS 1D (changing to greenish color as the bract ages).
*Bract color, both surfaces.*—RHS 1D.
*Bract petiole.*—Length: 1.0 cm to 3.0 cm. Diameter: 0.2 cm to 0.3 cm. Color, both surfaces: RHS 144B to RHS 144C.

Cyme:
*Diameter.*—1.0 cm to 2.0 cm.
*Cyathia number.*—4 to 6 per inflorescence.
*Cyathium.*—Shape: Ovate. Diameter: 0.3 cm to 0.4 cm. Length: 0.4 cm to 0.7 cm. Color: RHS 143A.
*Peduncle.*—Color: RHS 143A. Length: 0.1 cm to 0.2 cm.
*Nectar cups.*—Number: 1 to 2 per cyathia. Diameter: 0.1 cm. Length: 0.2 cm. Color: RHS 144B to RHS 144C.

Reproductive organs:
*Stamens.*—Quantity: 5 to 10 per cyathia. Shape: Ovate. Filaments: Color: RHS 1D. Length: 0.3 cm. Pollen: Quantity: Moderate. Color: RHS 9A.
*Gynoecium.*—Present.

Fruit and seed set: No fruit or seed have been observed

Disease and insect/pest resistance: Typical for the species

COMPARISON WITH PARENTAL AND COMMERCIAL CULTIVARS

'NPCW08119' differs from the parental poinsettia plant 'NPCW02044' (U.S. Plant Pat. No. 14,618) by having smaller foliage and smaller bracts than 'NPCW02044'. In addition, 'NPCW08119' has white bracts while 'NPCW02044' has red bracts.

'NPCW08119' differs from the commercial cultivar 'Gala White' (U.S. Plant Pat. No. 17,979) by having a narrower plant habit, fewer branches and a different shade of white bract color than 'Gala White'.

We claim:

1. A new and distinct cultivar of poinsettia plant as shown and described herein.

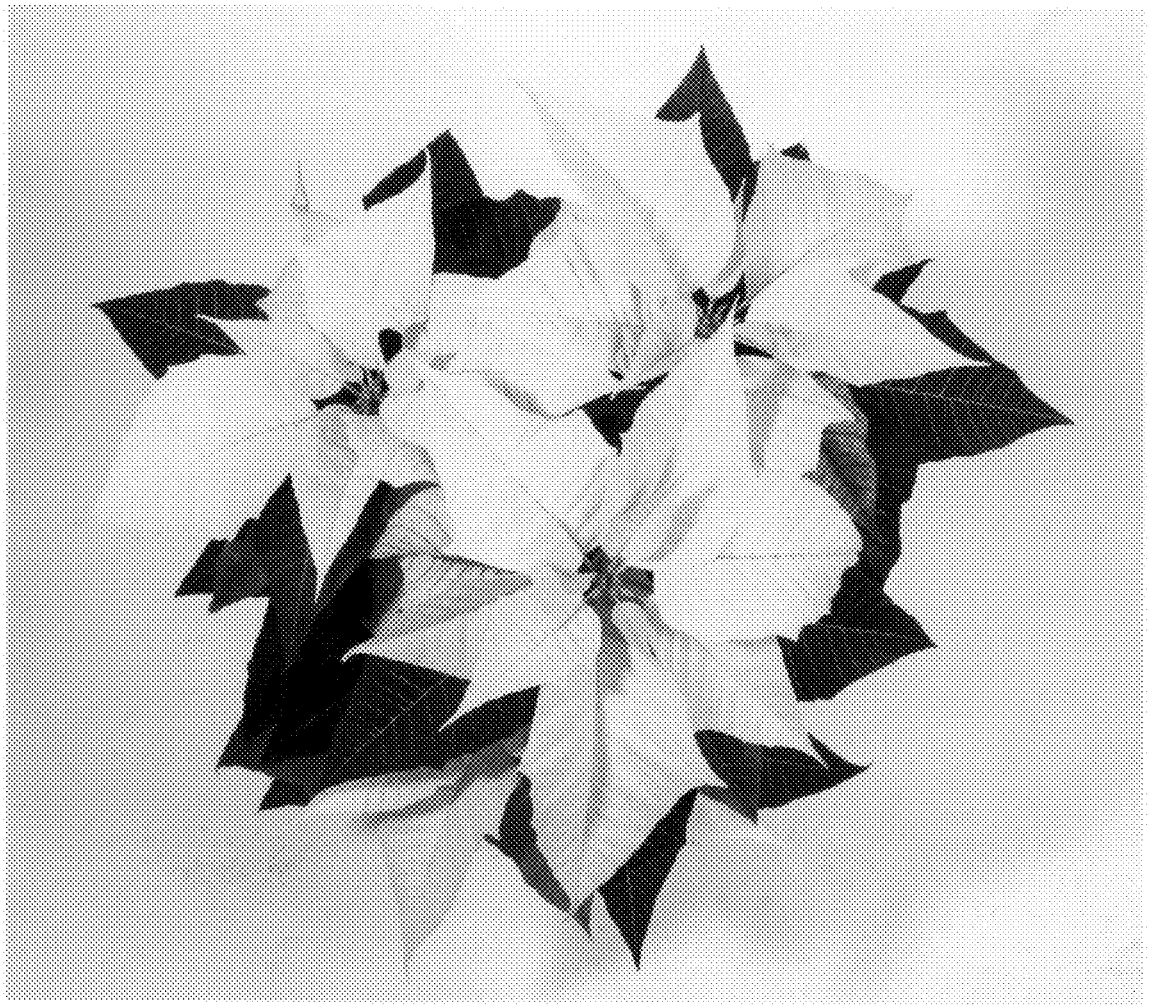

* * * * *